(12) United States Patent
Kopp et al.

(10) Patent No.: US 8,247,469 B2
(45) Date of Patent: Aug. 21, 2012

(54) DENTAL IMPRESSION MATERIAL

(75) Inventors: Markus Carsten Kopp, Constance (DE); Jürgen Fiedler, Constance (DE); Fuming Sun, Middletown (DE)

(73) Assignee: Dentsply International Inc., York, PA (US)

( * ) Notice: Subject to any disclaimer, the term of this patent is extended or adjusted under 35 U.S.C. 154(b) by 211 days.

(21) Appl. No.: 12/583,210

(22) Filed: Aug. 17, 2009

(65) Prior Publication Data
US 2011/0039973 A1 Feb. 17, 2011

(51) Int. Cl.
*A61K 6/093* (2006.01)
*C08G 77/12* (2006.01)
*A61C 9/00* (2006.01)
(52) U.S. Cl. ............... 523/109; 433/214; 528/14
(58) Field of Classification Search .......... 523/109; 433/214; 528/14
See application file for complete search history.

(56) References Cited

U.S. PATENT DOCUMENTS

| 3,453,242 | A | | 7/1969 | Schmitt et al. |
| 3,925,277 | A | * | 12/1975 | Lampe .................. 524/863 |
| 4,093,555 | A | | 6/1978 | Schmitt et al. |
| 4,167,618 | A | | 9/1979 | Schmitt et al. |
| 2007/0060717 | A1 | * | 3/2007 | Zech et al. ............... 525/478 |
| 2010/0304338 | A1 | * | 12/2010 | Cramer et al. ............ 433/202.1 |

FOREIGN PATENT DOCUMENTS

DE  1 544 837  4/1970

* cited by examiner

*Primary Examiner* — Tae H Yoon
(74) *Attorney, Agent, or Firm* — David A. Zdurne; Douglas J. Hura; Leana Levin

(57) ABSTRACT

Dental article for preparing a dental impression comprising
(i) a first paste composition, and
(ii) a second paste composition reactive upon mixing with the first paste composition in a curing reaction, characterized in that the dental article is obtainable by forming a predetermined amount of the first paste composition and a predetermined amount of the second paste composition into a body wherein the first and second paste compositions are separated by an interface preventing mixing and curing of the first paste composition and the second past composition during storage of the dental article.

16 Claims, 2 Drawing Sheets

DENTAL IMPRESSION MATERIAL

FIELD OF THE INVENTION

The present invention relates to a dental article for preparing a dental impression. Moreover, the present invention also relates to a kit of parts comprising the dental article of the invention. Finally, the present invention relates to a use of the dental article according to the invention for the preparation of a curable dental impression material.

BACKGROUND OF THE INVENTION

Dental impression materials are conventionally used for the preparation of dental impressions of the dental arch of a patient. Especially, dental impression materials for high precision impressions are conventionally based on silicone or polyether highly viscous pastes which are placed as tray material on the base of an impression tray shaped to the dental arch, and surround the preparation of the teeth. The impression material is usually prepared by mixing at least two components for forming a curable composition. The impression tray provided with the impression material assembly is then placed in the mouth and manually applied onto the dental arch for a period of several minutes. The impression tray and the material are then removed from the mouth and sent to the dental technician who will produce the final prosthesis.

The dosing of the components of the dental impression material is inherently problematic with conventional dental impression materials. Specifically, in case the dental practitioner has to determine and to provide specific amounts of the reactive components, errors are likely to occur. Moreover, even if standardized amounts are used, it is unavoidable that in many cases significant amounts of excess impression material is wasted. Finally, in case of a highly viscous paste, these problems are further aggravated since extrusion and mixing with a syringe through a static mixing element becomes impossible in view of the required extrusion force.

SUMMARY OF THE INVENTION

It is the problem of the present invention to provide a dental article for preparing a dental impression, which may be easily handled during storage and use, which allows quick, easy and efficient dosing of the components and which provides a dental impression material having superior, predictable and constant quality.

This problem is solved according to the invention with a dental article for preparing a dental impression comprising
(i) a first paste composition (B composition), and
(ii) a second paste composition (C composition) reactive upon mixing with the first paste composition in a curing reaction, characterized in that
the dental article is obtainable by forming a predetermined amount of the first paste composition and a predetermined amount of the second paste composition into a body wherein the first and second paste compositions are separated by an interface preventing mixing and curing of the first paste composition and the second past composition during storage of the dental article.

The interface separating the first and second paste compositions is incorporated into the dental impression material upon mixing of the paste compositions so that a homogeneous impression material is obtained including any component of the interface.

The present invention also provides a kit of parts comprising the dental article of the invention and a measuring device for determining a standard amount of dental impression material.

Finally, the present invention provides the use of the dental article of the invention for the preparation of a curable dental impression material.

DETAILED DESCRIPTION OF PREFERRED EMBODIMENTS

Figure 1:
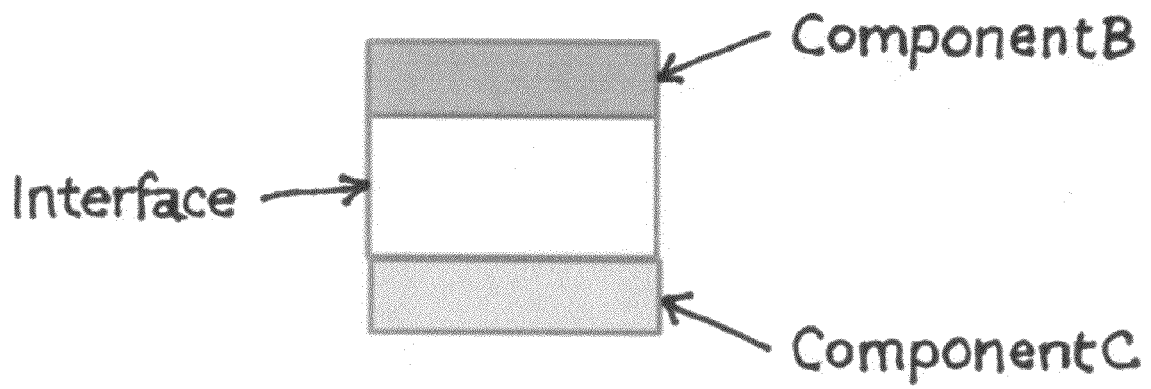
FIG. 1 shows a dental article of the present invention wherein the components are provided in layers separated by a non-reactive interface.

The dental article for preparing a dental impression comprises a first paste composition, and a second paste composition. The second paste composition is reactive upon mixing with the first paste composition in a curing reaction. The curing reaction may be based on an addition reaction and/or a condensation reaction.

An example for an addition reaction is the transition metal catalyzed hydrosilylation of carbon-carbon double bonds. Accordingly, the first paste composition may contain a organopolysiloxane compound and a transition metal catalyst. The second paste composition may contain a organohydrogenpolysiloxane compound. Both pastes may contain further components including fillers, alkyl substituted polysiloxanes, and additives such as pigments, hygroscopic agents, hydrogen absorbing agents, and plasticizing agents.

The organopolysiloxane used in the first paste may have at least two silicon-bonded aliphatic unsaturated hydrocarbon moieties per molecule thereof. The organopolysiloxane may have a straight-chain, branched, cyclic or network structures. Preferably, the organopolysiloxane has a straight-chain structure.

The aliphatic unsaturated hydrocarbon moieties include, for example, C1-C6 alkenyl groups such as vinyl, allyl, butenyl, pentenyl, and hexenyl. Preferably, a vinyl group is used.

Silicon-bonded organic moieties other than the aliphatic unsaturated hydrocarbon moieties include, for example, saturated monovalent C1-C10 hydrocarbon moieties including C1-C8 alkyl moieties such as methyl, ethyl, and propyl, C6-C10 aromatic hydrocarbon moieties such as phenyl and tolyl, C5-C10 alicyclic hydrocarbon moieties such as cyclopentyl, cyclohexyl and cycloheptyl. Of these organic moieties, methyl and phenyl are preferred.

Accordingly, the organopolysiloxane used in the dental article according to the present invention is preferably a linear chain organopolysiloxane having at least two aliphatic unsaturated hydrocarbons per molecule. Preferably, the organopolysiloxane is terminated with vinylsilyl groups at both ends of a molecular chain. Further, while an organosiloxane molecular chain includes an alkyl group, such as a methyl group and an ethyl group, a phenyl group, and a tolyl group, a methyl group and a phenyl group are especially preferred. Particularly preferred examples of the organopolysiloxane of the first paste include those in which all of the substituents other than the aliphatic unsaturated hydrocarbon moieties are methyl moieties, or an admixture of methyl and phenyl moieties.

The viscosity of the organopolysiloxane of the first paste measured with an oscillation/rotation rheometer in a creep test (constant strain or stress) at 25° C. is generally 10 Pa.s or above, preferably from 10 to 200 Pa.s.

The transition metal catalyst may be a platinum family metal catalyst as conventionally used for addition-curing type curable silicone compositions. Examples of the catalyst are platinum black, platinum supported on silica, carbon black, alcohol-modified chloroplatinic acids, chloroplatinic acid, platinum-vinylsiloxane complexes, or chloroplatinic acid-olefin complexes. In a preferred embodiment, a silicone-soluble platinum compound is used as an additive reaction catalyst, such as chloroplatinic acid, alcohol-modified chloroplatinic acid, and a complex of chloroplatinic acid and olefin. The silicone-soluble platinum compound is preferably dissolved with an alcohol-based, ketone-based, ether-based, or hydrocarbon-based solvent, or polysiloxane oil. The transition metal catalyst may be stabilized with an appropriate stabilizer.

The amount of the transition metal is appropriately adjusted so as to obtain a desired curing rate. In general, the amount of platinum is from 0.1 to 500 ppm, preferably from 1 to 300 ppm, based on organopolysiloxane.

The organohydrogenpolysiloxane used in the second paste may have at least three silicon-bonded hydrogen atoms in its molecule. The organohydrogenpolysiloxane may have any of straight-chain, branched, cyclic and network structures, of which the straight-chain structure is preferred. The organohydrogenpolysiloxane is used as a crosslinking agent for the organopolysiloxane.

In the curing reaction, the addition reaction is performed between the silicon-bonded hydrogen atom in the organohydrogenpolysiloxane and the aliphatic unsaturated hydrocarbon radical in the organopolysiloxane mentioned above, whereby a cured product is formed.

In the organohydrogenpolysiloxane, silicon-bonded organic moieties other than the silicon-bonded hydrogen atoms include, for example, $C_1$-$C_{10}$ saturated monovalent hydrocarbon moieties as exemplified above as one of substituents in the organopolysiloxane.

The content of the organohydrogenpolysiloxane is 0.1 to 50 weight parts per each paste with respect to 100 weight parts of the organopolysiloxane. When the content is less than 0.1 weight parts, setting speed of the silicone composition is slow. When the content is more than 50 weight parts, the set body of a silicone composition becomes brittle. More preferably, the content is 1 to 20 weight parts.

The viscosity of the organohydrogenpolysiloxane at 25° C. is generally from 0.005 to 100 Pa.s, preferable from 10 to 100 Pa.s.

The amount of organohydrogenpolysiloxane used in the dental article of the present invention is generally selected so that the number of the silicon-bonded hydrogen atoms in the organohydrogenpolysiloxane per one aliphatic unsaturated hydrocarbon radical in organopolysiloxane is preferably from 0.5 to 10, more preferably from 0.75 to 5. If the amount of organohydrogenpolysiloxane used is too large, the cured product of the composition obtained would be brittle or an excess of hydrosilyl moieties might be left in the cured product, causing changes in properties with time. If the amount is too small, on the other hand, unsatisfactory cure of the composition could result.

In a preferred embodiment, a surface active agent may be incorporated in the first paste and/or in the second paste. The surface active agent may have a siloxane unit and at least one, preferable from 3 to 150, hydrogen atoms or aliphatic unsaturated hydrocarbon moieties in the form of being bonded to a silicon atom of the siloxane unit, in its molecule. Accordingly, the cured product obtained from the dental article of the present invention retains the hydrophilic property for a long time, is excellent in physical properties such as dimensional stability, and is effectively free from the problems such as bleeding of the nonionic surface active agent to the surface of the cured product.

In the dental article for preparing a dental impression, if required, additives which are known per se, for instance, fillers, dyes, pigments, reinforcing agents, metallic powder, perfumes, fluidity-controlling agents, plasticizers, reaction retarders, can be blended insofar as the additives do not impair the hydrophilicity and the physical properties such as dimensional stability of the cured products obtained from the composition.

For instance, reinforcing fillers include fumed silica, precipitated silica, powdered quartz, powder of fused quartz, diatomaceous earth, or calcium carbonate. Preferably, the filler is fine silica powder. A filler may be present in the first paste and/or the second paste.

The dental article of the present invention may contain fine silica powder having a BET specific surface area of 50 to 500 $m^2$/g and being subjected to a hydrophobic treatment on the surface thereof. The hydrophobic silica can be obtained by subjecting fumed silica to a heat treatment with a surface treating agent such as methyltrichlorosilane, dimethyldichlorosilane, trimethylchlorosilane, alkoxysilane corresponding to those, octamethylcyclotetrasiloxane, hexamethyldisiloxane, hexamethyldisilane, or a mixture of those, or those surface treating agents with water.

A further example is a polyether impression material consisting of polyalkylene oxides, in which the end groups are derivatized with polymerizable like aziridines as disclosed in U.S. Pat. Nos. 3,453,242, 4,093,555, and DE-A 1 544 837. For the initiation of the polymerization, sulphonium salts are known from U.S. Pat. No. 4,167,618.

In order for a curing reaction to occur, a reactive component is required to have at least two reactive groups which may take part in a curing reaction. Preferably, at least one of the reactive components has three or more reactive groups so that crosslinking may occur.

Generally, the dental article for preparing a dental impression according to the invention is obtainable by forming a predetermined amount of the first paste composition and a predetermined amount of the second paste composition into a body wherein the first and second paste compositions are separated by an interface preventing mixing and curing of the first paste composition and the second paste composition during storage of the dental article.

The dental article of the present invention may be prepared by a moulding process wherein the first paste and the second paste, and optionally one or more further pastes are extruded and combined so as to provide an interface which prevents mixing and curing of reactive components of the first paste composition such as a reactive organopolysiloxane and reactive components of the second paste composition such as the organohydrogenpolysiloxane and/or the transition metal catalyst during storage of the dental article. If necessary, a suitable interlayer having a predetermined thickness and composition is provided between the first paste and the second paste. The interlayer of a predetermined thickness and composition, which separates the first and second paste compositions is incorporated into the dental impression material upon mixing of the paste compositions so that a homogeneous impression material is obtained including any component of the interlayer.

According to a preferred embodiment, the dental article of the present invention may be considered as a two-pack type composition comprising a part which contains an organopolysiloxane and another part which contains an organohydrogenpolysiloxane, and the two parts are only mixed with each other to effect curing at the time of use.

In order to avoid premature curing, the dental article may comprise a reaction retarder. The reaction retarder may be selected from acetylene alcohols, siloxane-modified acetylene alcohols, high-vinyl-content organopolysiloxanes such as tetravinyltetramethylcyclotetrasiloxane, or triallyl isocyanurate.

The dental article of the present invention is capable of being transformed into a dental impression material and cured in a short time at room temperature or by heating.

The cured products obtained from the composition of this invention are excellent in properties such as dimensional stability, and are free of bleeding of the nonionic surface active agent to the surface thereof even when the dental article is stored for a prolonged period of time. The dental article of the present invention, when used upon mixing in a moist atmosphere such as the inside of an oral cavity, is capable of forming an accurate impression, and are therefore especially suitable for use as a dental impression material.

The dental article according to the invention is preferably a stock material having a longitudinal axis wherein the ratio of the amounts of the first paste composition and the second paste composition of any segment cut perpendicularly to the longitudinal axis is constant. In a preferred embodiment, the ratio corresponds to a predetermined mixing ratio of the first and second paste compositions.

In a preferred embodiment, the dental article is in the form of a sheet having a cross section with a first layer consisting essentially of the first paste composition and a second layer consisting essentially of the second paste composition. The first layer and the second layer may be separated by an interlayer.

In a further preferred embodiment, the dental article is in the form of a rod having a cross section with a central portion consisting essentially of the first paste composition and a peripheral portion consisting essentially of the second paste composition.

In a further preferred embodiment, the dental article according to the present invention comprises an interface separating the first and second paste composition which is a paste layer preventing diffusion between the first paste composition and the second paste composition. For this purpose, the paste layer of the dental article may contain a retarder or inhibitor component.

The interlayer between the two reactive components of the dental article may comprise one or two components as follows:
(i) a retarder or inhibitor layer, retarding reaction between the first paste composition and the second paste composition by preventing migration of the reactive components of the first paste composition and the second paste composition, and
(ii) optionally a separation layer composition for keeping sufficient distance between the first paste composition and the second paste composition The inhibitor layer may comprise one or more organopolysiloxane compounds which do not take part in the curing reaction. Preferably, an organopolysiloxane terminated with trimethylsilyl groups at both ends of a molecular chain or short chained vinyldialkyldimetyl terminated siloxanes, such as divinyltetramethyldisiloxane or cyclic oligoalkylvinylsiloxanes such as tetramethyltetravinylcyclotetrasiloxane may be used. Conventional additives, such as fillers, dyes, pigments, reinforcing agents, metallic powder, perfumes, fluidity—controlling agents, and plasticizers may also be used in the inhibitor layer.

The separation layer may comprise for example organopolysiloxanes terminated with vinylsilyl groups at both ends of a molecular chain together with additives such as fillers, dyes, pigments, reinforcing agents, metallic powder, perfumes, fluidity—controlling agents, and plasticizers.

The thickness of the separator layer is preferably selected from a range of between 0.5-5.0 cm in order to minimize migration of the reactive components. More preferably, the thickness is 1 to 3 cm.

In order provide uniform mixing properties, it is preferred that all components including the first and second paste compositions have essentially the same viscosity at 23° C. Preferably, the difference in viscosity of any paste other than the first paste from the first paste is less than 10 percent based on the viscosity of the first paste.

The dental article according to the invention preferably comprises markings for indicating a predetermined amount of a dental impression material, whereby the markings are provided on the outer surface of a paste, or on a film provided on the outer surface of a paste.

The dental article may be packaged in a pouch. Filling of the dental article into the pouch may be carried out by extruding the components. In particular, the components may be extruded in a concentric arrangement into the pouch by using an extruder applicable for two or more components.

The present invention further provides a kit of parts comprising the dental article according to the invention and a measuring device for determining a standard amount of dental impression material.

The dental article according to the invention may be used for the preparation of a curable dental impression material.

EXAMPLES

The following compositions were prepared whereby percentages mean percent by weight unless indicated otherwise. Viscosity indications relate to dynamic viscosities as measured at 23° C. by the use of an oscillation/rotation rheometer.

Example 1

Figure 2:
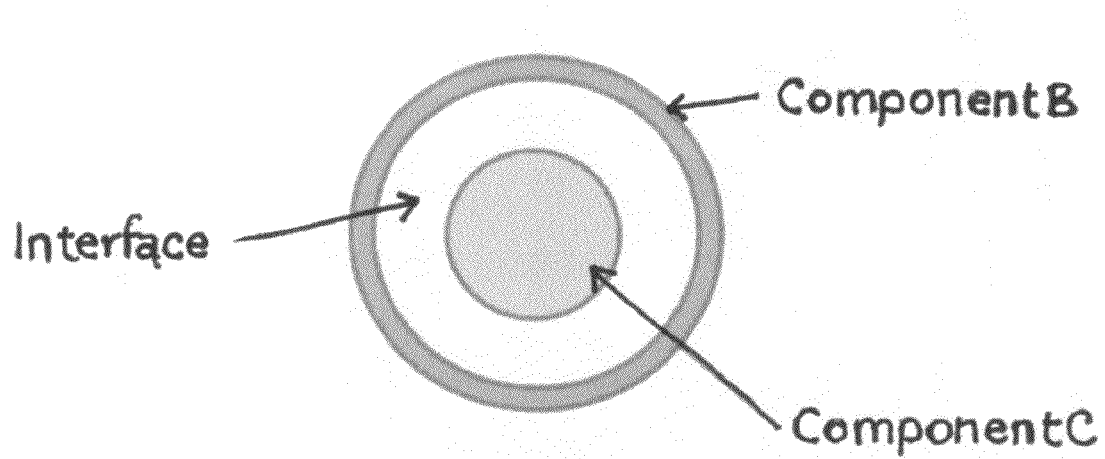
FIG. 2 shows a dental article of the present invention wherein the first and second pastes are formed into a rod. The first paste (C) represents the core of the rod and extends along the longitudinal axis. The second paste (B) represents an outer coating of the first paste and extends over the outer surface of the first paste. Both components (B) and (C) are separated by an interface layer (I).

The following pastes of Component B, Component C and Component I were prepared. Subsequently, equal parts by weight were arranged into a dental article resembling a rod or cable as shown in FIG. 2, whereby the cross-sectional dimensions of the article were as follows:

Diameter of Component C (grey): 29.0±0.2 mm
Thickness of Inhibitor layer I (white) 6.0±0.5 mm
Thickness of Component B (blue): 4.6±0.5 mm
Total diameter: 50.0±1.0 mm Moreover, a layered arrangement as shown in FIG. 1 wherein the thickness of component B, C and I was 13.33±0.5 mm, respectively and which had a total thickness 40.0±1.0 mm was also prepared.

Component B:

| | |
|---|---|
| 5.0% | trimethylsilyl end-capped polydimethyl-(H-methyl)-siloxane (SiH-content 4.3 mmol/g) |
| 25.07% | dimethylvinyl term. polydimethylsiloxane, (viscosity ☐ = 165 Pa · s) |

-continued

| | |
|---|---|
| 8.37% | dimethylvinylsilyl term. polydimethylsiloxane containing QM resins ($\square$ = 60,000 mPa · s) |
| 4.21% | zeolite type A alkali alumino silicate |
| 28.90% | silicon dioxide, cristobalite modification |
| 19.85% | silicon dioxide, amorphous (diatomaceous earth) |
| 2.98% | benzyl-octylphthlate |
| 1.0% | silicone glycol surfactant, low molecular weight |
| 4.46% | fumed silica |
| 0.15% | Iron red pigment |

Component C:

| | |
|---|---|
| 25.80% | dimethylvinyl term. polydimethylsiloxane, ($\square$ = 165 Pa · s) |
| 15.72% | dimethylvinylsilyl term. polydimethylsiloxane containing QM resins ($\square$ = 60,000 mPa · s) |
| 4.17% | zeolite type A alkali alumino silicate |
| 26.74% | silicon dioxide, cristobalite modification |
| 19.66% | silicon dioxide, amorphous (diatomaceous earth) |
| 2.95% | benzyl-octylphthlate |
| 0.2% | Pt/CaCO$_3$ 5%, dispersed in silicon dioxide |
| 0.1961% | Pt-Catalyst 2% in dimethylvinyl end-capped polydimethylsiloxane |
| 4.41% | fumed silica surface treated |

Component I (inhibitor):

| | |
|---|---|
| 26.85% | dimethylvinyl end-capped polydimethylsiloxane, ($\square$ = 165 Pa · s) |
| 15.51% | dimethylvinylsilyl end-capped polydimethylsiloxane containing QM resins ($\square$ = 60,000 mPa · s) |
| 4.12% | zeolite type A alkali alumino silicate |
| 29.26% | silicon dioxide, cristobalite modification |
| 19.38% | silicon dioxide, amorphous (diatomaceous earth) |
| 2.91% | benzyl-octylphthlate |
| 0.0076% | tetramethyltetravinylcyclotetrasiloxane |
| 4.34% | fumed silica, surface treated |
| 0.14% | iron oxide pigment |

Example 2

Dental articles having the same structure as shown in FIG. 1 and FIG. 2 as described in Example 1 were prepared based on the following components.

Component B:

| | |
|---|---|
| 6.0% | trimethylsilyl end-capped polydimethyl-(H-methyl)-siloxane (SiH-content 4.3 mmol/g) |
| 25.05% | dimethylvinyl end-capped polydimethylsiloxane, ($\square$ = 165 Pa · s) |
| 6.7% | dimethylvinylsilyl end-capped polydimethylsiloxane containing QM resins ($\square$ = 60,000 mPa · s) |
| 4.17% | zeolite type A alkali aluminosilicate |
| 29.26% | silicon dioxide, cristobalite modification |
| 19.88% | silicon dioxide, amorphous (diatomaceous earth) |
| 2.98% | benzyl-octylphthlate |
| 1.2% | silicone glycol surfactant, low molecular weight |
| 4.57% | fumed silica surface treated |
| 0.18% | Iron red pigment |

Component C:

| | |
|---|---|
| 25.80% | dimethylvinyl end-capped polydimethylsiloxane, ($\square$ = 165 Pa · s) |
| 15.72% | dimethylvinylsilyl end-capped polydimethylsiloxane containing QM resins ($\square$ = 60,000 mPa · s) |
| 4.17% | zeolite type A alkali aluminosilicate |
| 26.89% | silicon dioxide, cristobalite modification |
| 19.66% | silicon dioxide, amorphous (diatomaceous earth) |
| 2.95% | benzyl-octylphthlate |
| 0.2% | Pt/CaCO$_3$ 5%, dispersed in silicon dioxide |
| 0.1961% | Pt-Catalyst 2% in dimethylvinyl endcapped polydimethylsiloxane |
| 4.41% | surface treated fumed silica |

Component I (inhibitor):

| | |
|---|---|
| 27.43% | dimethylvinyl end-capped polydimethylsiloxane, ($\square$ = 165 Pa · s) |
| 15.10% | dimethylvinylsilyl end-capped polydimethylsiloxane containing QM resins ($\square$ = 60,000 mPa · s) |
| 4.02% | zeolite type A alkali aluminosilicate |
| 26.61% | silicon dioxide, cristobalite modification |
| 19.27% | silicon dioxide, amorphous (diatomaceous earth) |
| 2.89% | benzyl-octylphthlate |
| 0.0102% | tetramethyltetravinylcyclotetrasiloxane |
| 4.48% | surface treated fumed silica |
| 0.19% | iron oxide pigment |

Example 3

Dental articles having the same structure as shown in FIG. 1 and FIG. 2 as described in Example 1 were prepared based on the following components.

Component B:

| | |
|---|---|
| 6.0% | trimethylsilyl end-capped polydimethyl-(H-methyl)-siloxane (SiH-content 4.3 mmol/g) |
| 25.05% | dimethylvinyl end-capped polydimethylsiloxane, ($\square$ = 165 Pa · s) |
| 6.7% | dimethylvinylsilyl end-capped polydimethylsiloxane containing QM resins ($\square$ = 60,000 mPa · s) |
| 4.17% | zeolite type A alkali alumino silicate |
| 29.26% | silicon dioxide, cristobalite modification |
| 19.88% | silicon dioxide, amorphous (diatomaceous earth) |
| 2.98% | benzyl-octylphthlate |
| 1.2% | fumed silica |
| 4.57% | fumed silica surface treated |
| 0.18% | Iron red pigment |

Component C:

| | |
|---|---|
| 26.03% | dimethylvinyl end-capped polydimethylsiloxane, ($\square$ = 165 Pa · s) |
| 15.38% | dimethylvinylsilyl end-capped polydimethylsiloxane containing QM resins ($\square$ = 60,000 mPa · s) |
| 4.09% | zeolite type A alkali alumino silicate |
| 26.81% | silicon dioxide, cristobalite modification |
| 19.64% | silicon dioxide, amorphous (diatomaceous earth) |
| 2.95% | benzyl-octylphthlate |
| 0.26% | Pt/CaCO$_3$ 5%, dispersed in silicon dioxide |
| 0.2614 | Pt-Catalyst 2% in dimethylvinyl end-capped polydimethylsiloxane |
| 4.58% | fumed silica surface treated |

Component I (inhibitor):

| | |
|---|---|
| 26.85% | dimethylvinyl end-capped polydimethylsiloxane, (□ = 165 Pa·s) |
| 15.51% | dimethylvinylsilyl end-capped polydimethylsiloxane containing QM resins (□ = 60,000 mPa·s) |
| 4.12% | zeolite type A alkali alumino silicate |
| 29.26% | silicon dioxide, cristobalite modification |
| 19.38% | silicon dioxide, amorphous (diatomaceous earth) |
| 2.91% | benzyl-octylphthlate |
| 0.0076% | tetramethyltetravinylcyclotetrasiloxane |
| 4.57% | fumed silica surface treated |
| 0.14% | iron oxide pigment |

Example 4

The following pastes of Component B, Component C and Component I were prepared. Subsequently, parts by weight in a weight ratio of 1:1:2 of the Component B, Inhibitor layer I, and Component C, respectively, were arranged into a dental article resembling a cable having various length as shown in FIG. 2, whereby the cross-sectional dimensions of the article were as follows:

Diameter of Component C (grey): 35.5±0.5 mm
Thickness of Inhibitor layer I (white) 4.0±0.2 mm
Thickness of Component B (blue): 3.35±0.15 mm
Total diameter: 50.0±1.0 mm Moreover, a layered arrangement as shown in FIG. 1 wherein the thickness of component B, C and 110.0±0.5 mm, 10.0±0.5 mm, and 20.0±0.5 mm, respectively, and which had a total thickness 40.0±1.0 mm was also prepared.

Component B:

| | |
|---|---|
| 10.0% | trimethylsilyl end-capped polydimethyl-(H-methyl)-siloxane (SiH-content 4.3 mmol/g) |
| 20.0% | dimethylvinyl end-capped polydimethylsiloxane, rubber |
| 10.0% | dimethylvinylsilyl end-capped polydimethylsiloxane containing QM resins (□ = 60,000 mPa·s) |
| 4.0% | calcium sulphate, dried |
| 5.0% | ethoxylated nonylphenol |
| 22.3% | silicon dioxide, cristobalite modification |
| 20.0% | silicon dioxide, amorphous (diatomaceous earth) |
| 5.4% | benzyl-octylphthlate |
| 3.0% | fumed silica surface treated |
| 0.30% | iron oxide pigment |

Component C:

| | |
|---|---|
| 10.0% | dimethylvinyl end-capped polydimethylsiloxane, rubber |
| 33.7% | dimethylvinylsilyl end-capped polydimethylsiloxane containing QM resins (□ = 60,000 mPa·s) |
| 5.0% | calcium sulphate, dried |
| 25.8% | silicon dioxide, cristobalite modification |
| 14.0% | silicon dioxide, amorphous (diatomaceous earth) |
| 4.5% | benzyl-octylphthlate |
| 1.0% | Pt/CaCO$_3$ 5%, dispersed in silicon dioxide |
| 1.0% | Pt-Catalyst 2% in dimethylvinyl end-capped polydimethylsiloxane |
| 5.0% | fumed silica surface treated |

Component I (inhibitor):

| | |
|---|---|
| 40.0% | dimethylvinylsilyl end-capped polydimethylsiloxane containing QM resins (□ = 60,000 mPa·s) |
| 6.0% | calcium sulphate, dried |
| 26.9% | silicon dioxide, cristobalite modification |
| 20.0% | silicon dioxide, amorphous (diatomaceous earth) |
| 3.6% | benzyl-octylphthlate |
| 0.2% | tetramethyltetravinylcyclotetrasiloxane |
| 3.0% | surface treated fumed silica |

Example 5

The following pastes of Component B, Component C and Component I were prepared. Subsequently, parts by weight in a weight ratio of 1:2:1 of the Component B, Inhibitor layer I, and Component C, respectively, were arranged into a dental article resembling a cable having various length as shown in FIG. 2, whereby the cross-sectional dimensions of the article were as follows:

Diameter of Component C (grey): 25.0±0,5 mm
Thickness of Inhibitor layer I (white) 9.15±0,2 mm
Thickness of Component B (blue): 3.35±0,15 mm
Total diameter: 50.0±1.0 mm Moreover, a layered arrangement as shown in FIG. 1 wherein the thickness of component B, C and 110,0±0,5 mm, 10,0±0,5 mm, and 20,0±0,5 mm, respectively, and which had a total thickness 40,0±1,0 mm was also prepared.

Component B:

| | |
|---|---|
| 12.0% | trimethylsilyl end-capped polydimethyl-(H-methyl)-siloxane (SiH-content 4.3 mmol/g) |
| 30.0% | dimethylvinyl end-capped polydimethylsiloxane, rubber |
| 6.0% | dimethylvinylsilyl end-capped polydimethylsiloxane containing QM resins (□ = 60,000 mPa·s) |
| 5.0% | calcium sulphate, dried |
| 5.0% | ethoxylated nonylphenol |
| 19.7% | silicon dioxide, cristobalite modification |
| 14.0% | silicon dioxide, amorphous (diatomaceous earth) |
| 5.0% | benzyl-octylphthlate |
| 3.0% | fumed silica surface treated |
| 0.30% | Iron red pigment |

Component C:

| | |
|---|---|
| 9.43% | dimethylvinyl end-capped polydimethylsiloxane, rubber |
| 32.08% | dimethylvinylsilyl end-capped polydimethylsiloxane containing QM resins (□ = 60,000 mPa·s) |
| 4.72% | Calciumsulfate, dried |
| 24.53% | silicon dioxide, cristobalite modification |
| 13.21% | silicon dioxide, amorphous (diatomaceous earth) |
| 4.72% | benzyl-octylphthlate |
| 1.887% | Pt/CaCO$_3$ 5%, dispersed in silicon dioxide |
| 2.83% | Pt-Catalyst 2% in dimethylvinyl end-capped polydimethylsiloxane |
| 6.6% | surface treated fumed silica |

Component I (inhibitor):

| | |
|---|---|
| 42.0% | dimethylvinylsilyl end-capped polydimethylsiloxane containing QM resins (□ = 60,000 mPa·s) |
| 5.0% | calcium sulfate, dried |
| 25.55% | silicon dioxide, cristobalite modification |
| 20.0% | silicon dioxide, amorphous (diatomaceous earth) |
| 4.0% | benzyl-octylphthlate |
| 0.15% | tetramethyltetravinylcyclotetrasiloxane |
| 3.0% | surface treated fumed silica |

Example 6

The following pastes of Component B, Component C and Component I were prepared. Subsequently, parts by weight in a weight ratio of 1:8:1 of the Component B, Inhibitor layer I, and Component C, respectively, were arranged into a dental article resembling a cable having various length as shown in FIG. 2, whereby the cross-sectional dimensions of the article were as follows:

Diameter of Component C (grey): 15.7±0.2 mm
Thickness of Inhibitor layer I (white) 15.7±0.2 mm
Thickness of Component B (blue): 1.45±0.1 mm
Total diameter: 50.0±1.0 mm Moreover, a layered arrangement as shown in FIG. 1 wherein the thickness of component B, C and I 10.0±0.5 mm, 10.0±0.5 mm, and 20.0±0.5 mm, respectively, and which had a total thickness 40.0±1.0 mm was also prepared.

Component B:

| | |
|---|---|
| 28.0% | trimethylsilyl end-capped polydimethyl-(H-methyl)-siloxane (SiH-content 4.3 mmol/g) |
| 24.0% | dimethylvinyl end-capped polydimethylsiloxane, rubber |
| 5.0% | calcium sulphate, dried |
| 10.0% | ethoxylated nonylphenol |
| 25.7% | silicon dioxide, amorphous (diatomaceous earth) |
| 7.0% | surface treated fumed silica |
| 0.30% | Iron red pigment |

Component C:

| | |
|---|---|
| 12.0% | dimethylvinyl end-capped polydimethylsiloxane, rubber |
| 25.0% | dimethylvinylsilyl end-capped polydimethylsiloxane containing QM resins (☐ = 60,000 mPa · s) |
| 5.0% | calcium sulphate, dried |
| 26.0% | silicon dioxide, cristobalite modification |
| 14.0% | silicon dioxide, amorphous (diatomaceous earth) |
| 5.0% | benzyl-octylphthlate |
| 4.0% | Pt/CaCO$_3$ 5%, dispersed in silicon dioxide |
| 5.0% | Pt-Catalyst 2% in dimethylvinyl end-capped polydimethylsiloxane |
| 4.0% | surface treated fumed silica |

Component I (inhibitor):

| | |
|---|---|
| 38.0% | dimethylvinylsilyl end-capped polydimethylsiloxane containing QM resins (☐ = 60,000 mPa · s) |
| 8.0% | dimethylvinyl end-capped polydimethylsiloxane, rubber |
| 5.0% | calcium sulphate, dried |
| 24.64% | silicon dioxide, cristobalite modification |
| 16.0% | silicon dioxide, amorphous (diatomaceous earth) |
| 5.0% | benzyl-octylphthlate |
| 0.06% | tetramethyltetravinylcyclotetrasiloxane |
| 3.0% | surface treated fumed silica |

The results are shown in the following Table:

| Example | BIC Ratio | Working Time (min) | Setting Time (min) | Recovery (%) ISO 4823 | Strain (%) ISO 4823 | Tear Strength (PSI) |
|---|---|---|---|---|---|---|
| 1 | 1:1:1 | 2:25 | 4:45 | 97.20 | 2.50 | — |
| 2 | 1:1:1 | 1:30 | 3:10 | — | — | — |
| 3 | 1:1:1 | 2:10 | 4:15 | 98.40 | 1.90 | 307.2 (6.6) |
| 4 | 1:1:2 | 1:15 | 5:00 | 95.30 | 1.75 | |
| 5 | 1:2:1 | 1:30 | 5:45 | 96.80 | 1.35 | |
| 6 | 1:8:1 | 2:20 | 6:45 | 97.25 | 2.15 | |

The invention claimed is:

1. Dental article for preparing a dental impression comprising
   (i) a first paste composition, and
   (ii) a second paste composition reactive upon mixing with the first paste composition in a curing reaction, characterized in that the dental article is obtained by forming a predetermined amount of the first paste composition and a predetermined amount of the second paste composition into a body wherein the first and second paste compositions are separated by an interface preventing mixing and curing of the first paste composition and the second past composition during storage of the dental article, and
   wherein the interface separating the first and second paste composition is a paste layer preventing diffusion between the first paste composition and the second paste composition.

2. The dental article according to claim 1, wherein the curing reaction is based on an addition reaction, a condensation reaction, or both.

3. The dental article according to claim 1, wherein the first paste composition contains a organopolysiloxane compound and a transition metal catalyst.

4. The dental article according to claim 1, wherein the second paste composition contains a organohydrogenpolysiloxane compound.

5. The dental article according to claim 1, wherein the first paste, the second paste, or both contain a filler.

6. The dental article according to claim 1, wherein the dental article is an elongated body having a longitudinal axis and wherein the ratio of the amounts of the first paste composition and the second paste composition of any segment cut perpendicularly to the longitudinal axis is constant.

7. The dental article according to claim 6, wherein the ratio corresponds to a predetermined mixing ratio of the first and second paste compositions.

8. The dental article according to claim 1, wherein the dental article is in the form of a rod having a cross section with a central portion consisting essentially of the first paste composition and a peripheral portion consisting essentially of the second paste composition.

9. The dental article according to claim 1, wherein the paste layer contains (i) a retarder paste, or (ii) an inhibitor layer and/or retarder layer and an additional separation layer of sufficient thickness to prevent migration of reactive components between the first and second paste.

10. The dental article according to claim 1, wherein the first and second paste compositions have essentially the same viscosity at 23° C.

11. The dental article according to claim 1, which comprises markings for indicating a predetermined amount of a dental impression material, whereby the markings are provided on the outer surface of a paste, or on a film provided on the outer surface of a paste.

12. The dental article according to claim 1, which is packaged in a pouch.

13. Kit of parts comprising the dental article according to claim 1 and a measuring device for determining a standard amount of dental impression material.

14. A method of using the dental article according to claim 1 for the preparation of a curable dental impression material.

15. The dental article according to claim 1, wherein the paste layer includes one or more organopolysiloxane compounds which do not take part in the curing reaction.

16. The dental article according to claim 1, wherein the paste layer separating the first and second paste compositions is incorporated into the dental impression material upon mixing of the paste compositions so that a homogeneous impression material is obtained including any component of the interface.

* * * * *